(12) United States Patent
Lim (10) Patent No.: US 11,974,808 B2
(45) Date of Patent: May 7, 2024

(54) ANTERIOR EYE DISEASE DIAGNOSTIC SYSTEM AND DIAGNOSTIC METHOD USING SAME

(71) Applicant: SAMSUNG LIFE PUBLIC WELFARE FOUNDATION, Seoul (KR)

(72) Inventor: Dong Hui Lim, Seoul (KR)

(73) Assignee: SAMSUNG LIFE PUBLIC WELFARE FOUNDATION (KR)

( * ) Notice: Subject to any disclaimer, the term of this patent is extended or adjusted under 35 U.S.C. 154(b) by 705 days.

(21) Appl. No.: 17/251,478

(22) PCT Filed: May 29, 2019

(86) PCT No.: PCT/KR2019/095022
§ 371 (c)(1),
(2) Date: Dec. 11, 2020

(87) PCT Pub. No.: WO2019/240567
PCT Pub. Date: Dec. 19, 2019

(65) Prior Publication Data
US 2021/0244272 A1 Aug. 12, 2021

(30) Foreign Application Priority Data
Jun. 11, 2018 (KR) .................. 10-2018-0066936

(51) Int. Cl.
*A61B 3/117* (2006.01)
*A61B 3/00* (2006.01)
(Continued)

(52) U.S. Cl.
CPC ............ *A61B 3/117* (2013.01); *A61B 3/0025* (2013.01); *A61B 3/14* (2013.01); *A61B 5/7267* (2013.01);
(Continued)

(58) Field of Classification Search
CPC ..... A61B 3/117; A61B 3/0025; A61B 5/7267; G16H 50/50; G16H 50/20; G16H 30/20;
(Continued)

(56) References Cited

U.S. PATENT DOCUMENTS

2014/0276025 A1* 9/2014 Durbin .................. A61B 3/102
600/407
2017/0251985 A1* 9/2017 Howard ................. G16H 70/60
(Continued)

FOREIGN PATENT DOCUMENTS

JP 2006087614 A 4/2006
JP 2011200512 A 10/2011
(Continued)

OTHER PUBLICATIONS

PCT International Search Report for PCT/KR2019/095022; dated Sep. 6, 2019, 2 pages.
(Continued)

*Primary Examiner* — Gabriel I Garcia
(74) *Attorney, Agent, or Firm* — Dilworth IP, LLC (57) ABSTRACT

Provided is a diagnosis system for anterior eye diseases. An image obtainer obtains an anterior eye image of an image obtainer configured to obtain an anterior eye image of a subject. A characteristic extractor extracts characteristic information of the obtained anterior eye image on the basis of a machine-learning model. A disease analyzer determines whether or not an anterior eye of the subject has a disease and classifying a disease class according to the extracted characteristic information.

11 Claims, 6 Drawing Sheets

(51) Int. Cl.
  *A61B 3/14* (2006.01)
  *A61B 5/00* (2006.01)
  *G06N 3/08* (2023.01)
  *G06T 7/00* (2017.01)
  *G16H 30/20* (2018.01)
  *G16H 30/40* (2018.01)
  *G16H 50/20* (2018.01)
  *G16H 50/50* (2018.01)

(52) U.S. Cl.
  CPC ............. *G06N 3/08* (2013.01); *G06T 7/0012* (2013.01); *G16H 30/20* (2018.01); *G16H 30/40* (2018.01); *G16H 50/20* (2018.01); *G16H 50/50* (2018.01); *G06T 2207/20081* (2013.01); *G06T 2207/20084* (2013.01); *G06T 2207/30041* (2013.01); *G06T 2207/30096* (2013.01)

(58) Field of Classification Search
  CPC ........ G16H 30/40; G06N 3/08; G06T 7/0012; G06T 2207/20081; G06T 2207/20084; G06T 2207/30096
  USPC ........................................................ 382/128
  See application file for complete search history.

(56) References Cited

U.S. PATENT DOCUMENTS

2018/0315193 A1* 11/2018 Paschalakis ......... G06V 40/193
2019/0200861 A1* 7/2019 Solanki ................ A61B 3/0075
2019/0222817 A1* 7/2019 Abou Shousha ...... H04N 9/646

FOREIGN PATENT DOCUMENTS

| | | |
|---|---|---|
| JP | 2013169295 A | 9/2013 |
| KR | 20140108417 A | 9/2014 |
| KR | 101789166 B1 | 10/2017 |
| KR | 101848322 B1 | 4/2018 |

OTHER PUBLICATIONS

Written Opinion of the International Searching Authority for PCT/KR2019/095022; Applicant Samsung Life Public Welfare Foundation; dated Sep. 6, 2019, 7 pages.

International Preliminary Report on Patentability for PCT/KR2019/095022; Applicant Samsung Life Public Welfare Foundation; dated Dec. 15, 2020, 7 pages.

* cited by examiner

ANTERIOR EYE DISEASE DIAGNOSTIC SYSTEM AND DIAGNOSTIC METHOD
USING SAME

BACKGROUND

1. Technical Field

Exemplary embodiments of the present disclosure relate to a diagnosis system for anterior eye diseases and a diagnosis method using the same, and more particularly, to a diagnosis system for anterior eye diseases, the diagnosis system being configured to obtain an anterior eye image of a subject, extract characteristic information of the anterior eye image using a machine-learning model, and diagnose an anterior eye disease on the basis of the extracted characteristic.

2. Related Art

Anterior eye diseases are diagnosed by a doctor directly observing an anterior eye image using a slit lamp microscope. In a number of cases, it may be difficult for ophthalmologists to read the anterior eye image in spite of using slit lamp microscopes. Thus, there is a problem in that it is difficult to accurately diagnose anterior eye diseases.

Recently, a variety of algorithms using artificial intelligence technology have been developed. In particular, technologies for processing image data using a machine learning algorithm have been developed. These technologies have improved the accuracy of image analysis.

However, an assistance system to which an anterior eye image is input and which is configured to accurately determine an anterior eye disease using a machine learning model in order to assist in the diagnosis of anterior eye diseases has not yet been developed. Therefore, there is a need to develop a diagnostic assistance system for anterior eye diseases which improves the accuracy of image reading in order to provide appropriate treatment methods to patients.

DOCUMENTS OF BACKGROUND ART (Patent Document 1) Korean Patent Application Publication No. 10-1992-7000577 (published on Aug. 10, 1992)

SUMMARY

Various embodiments are directed to analyzing an anterior eye image by machine learning in order to improve the accuracy of diagnosis of anterior eye diseases, thereby facilitate the diagnosis.

The technical objectives of the present disclosure are not limited to the aforementioned description, and the other objectives not disclosed herein can be considered from embodiments of the present disclosure to be described below by those skilled in the art.

In an embodiment, a diagnosis system for anterior eye diseases may be provided.

The diagnosis system for anterior eye diseases according to an embodiment of the present disclosure may include: an image obtainer configured to obtain an anterior eye image of a an image obtainer configured to obtain an anterior eye image of a subject; a characteristic extractor configured to extract characteristic information of the obtained anterior eye image on the basis of a machine-learning model; and a disease analyzer configured to determine whether or not an anterior eye of the subject has a disease and classifying a disease class according to the extracted characteristic information.

The diagnosis system may further include a storage in which a previously-obtained anterior eye image of each of the subject and other subjects is stored. The anterior eye image of the subject may be obtained in real time for a diagnosis or be obtained by loading the anterior eye image stored in the storage.

The diagnosis system may further include an output unit configured to output medical information regarding whether or not the anterior eye of the subject has the disease and the disease class, which are determined and classified by the disease analyzer.

The characteristic information may include at least one of color information of a lesion, position information of the lesion, depth information of the lesion, blood vessel information of surrounding portions of cornea, surface information of conjunctiva, and surface information of sclera.

The machine learning model of the characteristic extractor may include a deep convolutional generative adversarial net. The output unit may output both the anterior eye image and image information regarding a lesion extracted in accordance with the machine learning model.

The medical information may include at least one of current state information of the anterior eye, future state prediction information of the anterior eye, and treatment information of the disease class.

In an embodiment, a diagnosis method using a diagnosis system for anterior eye diseases may be provided.

The diagnosis method using a diagnosis system for anterior eye diseases according to an embodiment of the present disclosure may include: obtaining an anterior eye image of a subject; extracting characteristic information of the obtained anterior eye image on the basis of a machine-learning model; and determining whether or not an anterior eye of the subject has a disease and classifying a disease class according to the extracted characteristic information.

The anterior eye image of the subject may be obtained in real time for a diagnosis or be obtained by loading an anterior eye image previously stored in a storage of the diagnosis system for anterior eye disease.

The diagnosis method of claim 7, further including outputting, by an output unit of the diagnosis system for anterior eye diseases, medical information regarding the classified disease class after the determining and classifying.

In an embodiment, a computer readable recording medium in which a program configured to realize the above-described method is recorded may be provided.

According to the present disclosure, it is possible to provide a diagnostic assistance system enabling an appropriate treatment method to be presented by improving the accuracy of the diagnosis of anterior eye diseases.

In addition, the present disclosure may not only be used as the assistance system helping an ophthalmologist to make an accurate diagnosis but also allow persons, such as a patient, without specialized knowledge to obtain diagnostic assistant information so that anterior eye diseases may be appropriately managed.

The effects obtainable from embodiments of the present disclosure are not limited to the aforementioned description, and the other effects not explicitly disclosed herein will be clearly derived and understood from the descriptions of the embodiments of the present disclosure to be described below by those skilled in the art. That is, non-intended effects which may be obtained by carrying out the present disclo-

DETAILED DESCRIPTION

Hereinafter, embodiments of the present disclosure will be described in detail with reference to the accompanying drawings so that those skilled in the art to which the present disclosure pertains could easily put the present disclosure into practice. However, the present disclosure may be realized in a variety of different forms and is not limited to embodiments to be described hereinafter. In order to clearly describe the present disclosure, portions irrelevant to the descriptions are omitted from the drawings. Like reference numerals designate like elements throughout the specification.

Terms used in the present specification will be briefly described before the present disclosure is described in detail.

As the terms used in the present disclosure, general terms which are widely used nowadays are selected in consideration of the functions thereof. However, the terms may be changed depending on the intention of those skilled in the art, the precedent, the appearance of new technique, or the like. In a specific case, a term selected by the present applicant may be used. In this case, the meaning of the term will be described in detail in the corresponding part of this specification. Therefore, the terms used herein should be defined not by the names of the terms, but by the meanings of the terms based on the overall disclosures set forth herein.

Throughout the specification, when an element is referred to as "including" a component, it will be understood that the element does not exclude another component unless referred to the contrary, but may further include another component. In addition, a term such as "portion," "unit," or "module" indicates a unit for processing at least one function or operation, and may be implemented using hardware, software, or a combination of hardware and software. It will be understood that when an element is referred to as being "connected" to another element, it can be "directly connected" to the other element, or "indirectly connected" to the other element via an "intervening" element.

Hereinafter, the present disclosure will be described in detail with reference to the drawings.

Figure 1:
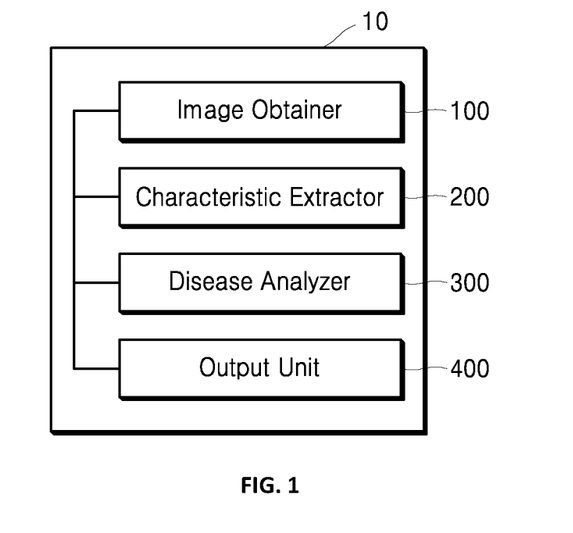
FIG. 1 is a block diagram illustrating a diagnosis system for anterior eye diseases according to an embodiment of the present disclosure.

FIG. 1 is a block diagram illustrating a diagnosis system 10 for anterior eye diseases according to an embodiment of the present disclosure. Referring to FIG. 1, the diagnosis system 10 for anterior eye diseases according to an embodiment of the present disclosure may include an image obtainer 100 configured to obtain an anterior eye image 20 of a subject, a characteristic extractor 200 configured to extract characteristic information of the obtained anterior eye image 20 on the basis of a machine learning model, and a disease analyzer 300 configured to determine whether or not the subject has an anterior eye disease and classify the disease class according to the extracted characteristic information.

The machine learning model according to an embodiment of the present disclosure may include a deep neural network (DNN). The DNN refers to a neural network having a deep structure. The DNN may be configured such that a structure comprised of a plurality of network layers learn a large amount of data so as to automatically learn the characteristic of signals and the relationship between signals, thereby diagnosing an anterior eye disease. In particular, a convolution neural network (CNN) may be used as a model for extracting characteristic in the anterior eye image 20.

Figure 2:
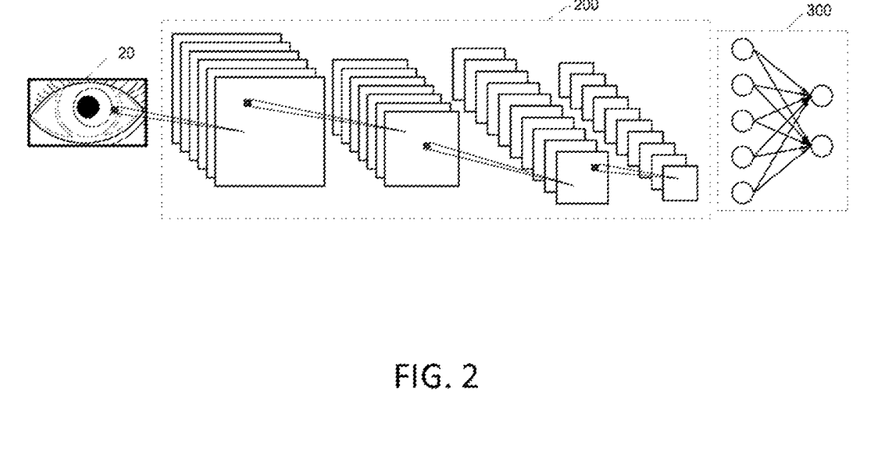
FIG. 2 is an example diagram illustrating the characteristic extractor and the disease analyzer of diagnosis system for anterior eye diseases according to an embodiment of the present disclosure.

The CNN is configured as illustrated in FIG. 2 such that the characteristic extractor 200 of the diagnosis system 10 for anterior eye diseases according to an embodiment of the present disclosure may extract the characteristic in the anterior eye image 20 and the disease analyzer 300 of the diagnosis system 10 may analyze an anterior eye disease on the basis of the extracted characteristic. The characteristic extractor 200 may include a convolution layer and a pooling layer, and the disease analyzer 300 may be designed as a fully-connected layer.

Specifically, the convolution layer of the characteristic extractor 200 may form a feature map by applying a plurality of filters to each area of the anterior eye image 20. The pooling layer may resize a specific map. In addition, the characteristic extractor 200 may be configured such that the convolution layers and the pooling layers are repeated several times. In addition, the fully-connected layer of the disease analyzer 300 may include a classification model, such as a multi-layer perceptron (MLP) or a support vector machine, and thus may predict an anterior eye disease by classifying the extracted characteristic.

The anterior eye disease analyzed by the disease analyzer 300 according to an embodiment of the present disclosure may be classified according to the structure of the anterior eye and the type of the disease. Regarding the structure of the anterior eye, the anterior eye may include the cornea, the conjunctiva, the sclera, the anterior chamber of the anterior eye, the lens, the iris, the ciliary body, and the like. In addition, examples of the anterior eye diseases may include infectious inflammatory diseases related to bacteria, virus, fungi, and other infections; non-infectious inflammatory diseases including autoimmunity or the like; non-inflammatory diseases including degeneration, dystrophy, keratoconus, and the like; and other diseases related to the anterior eye, such as dry eye disease, cataract, corneal erosion, deposit, edema, and corneal opacity. That is, types of anterior eye diseases may be classified into anterior eye diseases caused by infectious or non-infectious inflammations, non-inflammatory diseases, wounds, aging, and the like, according to the structure of the anterior eye. For example, when the conjunctiva in the structure of the anterior eye has a disease, the disease analyzer may classify the predicted anterior eye disease as one of conjunctiva diseases, such as conjunctiva infection and conjunctiva allergy.

In addition, the disease analyzer 300 according to an embodiment of the present disclosure may predict an anterior eye disease that is predicted with highest probability. The degree of progression of the corresponding anterior eye disease may be classified as the disease class. That is, the disease class may mean a grade classified on the basis of the degree of progression or severity of the anterior eye disease predicted by the disease analyzer 300. For example, the disease class may be expressed by a variety of methods able to express the degree of progression or severity of the disease. That is, the disease class may be indicated to be serious, intermediate, and mild, or may be expressed with predetermined numbers.

Figure 3:
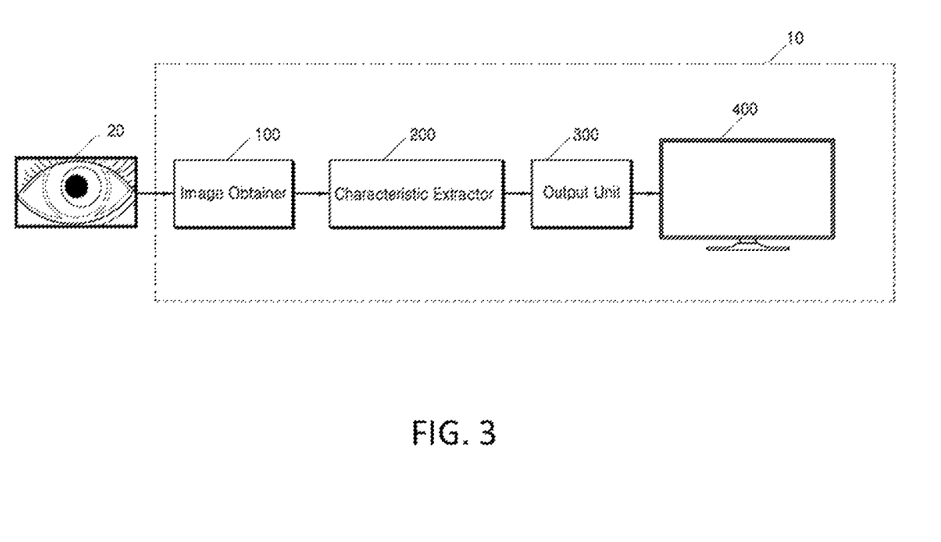
FIG. 3 is an example diagram illustrating a diagnosis process using the diagnosis system for anterior eye diseases according to an embodiment of the present disclosure.

FIG. 3 is an example diagram illustrating a diagnosis process using the diagnosis system 10 for anterior eye diseases according to an embodiment of the present disclosure.

The diagnosis system 10 for anterior eye diseases according to an embodiment of the present disclosure may further include a storage in which the anterior eye image 20 previously obtained from each of the subject and the other subjects is stored. The anterior eye image 20 of the subject may be obtained in real time for a diagnosis or be obtained by loading the anterior eye image 20 previously stored in the storage.

That is, the image obtainer 100 according to an embodiment of the present disclosure may obtain the anterior eye image 20 by capturing the anterior eye image 20 in real time through a device installed in a doctor's office or a hospital, or a user device. The anterior eye image 20 may be obtained in real time by being captured in a hospital or a doctor's office through a slit lamp microscope, but may also be obtained in real time by other devices configured to capture the anterior eye image 20. The user device is not limited as long as the user device is a device, such as a smartphone, a tablet computer, or a digital camera, which includes an image-capturing module and may capture the anterior eye image 20.

In addition, the image obtainer 100 may obtain the anterior eye image 20 by loading the anterior eye image 20 from the storage in which the anterior eye image 20 previously obtained from the subject is stored. Furthermore, the anterior eye images 20, previously obtained from the other subjects, may also be stored in the storage and be used as data for the learning of the machine learning model.

Figure 4:
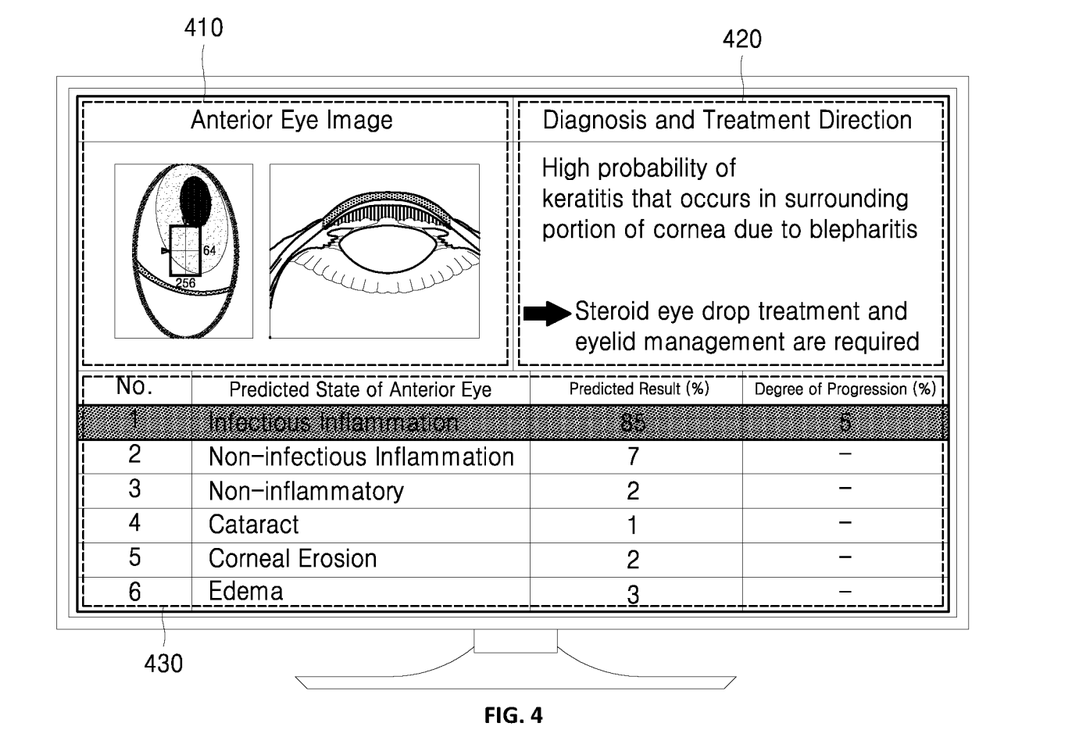
FIG. 4 is an example diagram illustrating the output unit of the diagnosis system for anterior eye diseases according to an embodiment of the present disclosure.

In addition, the anterior eye image 20 of the subject depending on the progression may be stored in the storage, and accordingly, the machine learning model for a diagnosis may be designed. That is, a pattern or an aspect of changes in the anterior eye image 20 over time may be stored in the storage and may be learned by the machine learning model. Thus, a diagnosis may be performed by predicting the anterior eye disease over time on the basis of the pattern or aspect of changes in the image. FIG. 4 is an example diagram illustrating an output unit 400 of the diagnosis system 10 for anterior eye diseases according to an embodiment of the present disclosure. Referring to FIG. 4, the diagnosis system 10 for anterior eye diseases according to an embodiment of the present disclosure may further include the output unit 400 configured to output whether or not the disease classified by the disease analyzer 300 has occurred, and medical information of the disease class. The medical information may include at least one of current state information of the anterior eye, future state prediction information of the anterior eye, and treatment information of the disease class.

Specifically, as illustrated in FIG. 4, the output unit 400 may display information divided into an anterior eye image frame 410 of the anterior eye image 20, a diagnosis and treatment direction frame 420, and a diagnosis and analysis frame 430.

In the anterior eye image frame 410, the anterior eye image 20 may be displayed in a variety of methods. That is, the anterior eye image 20 captured in front of the anterior eye may be output, and the anterior eye image 20 obtained from a side portion of the anterior eye may be output. In addition, a detected lesion may be simultaneously displayed on the obtained anterior eye image 20 while being highlighted, thereby allowing a user, such as a doctor, to easily check the location of the lesion.

The diagnosis and treatment direction frame 420 shows a result of the diagnosis and a treatment direction. The result of the diagnosis and the treatment direction may not only be displayed with text, as illustrated in FIG. 4, but also be expressed as images. The diagnosis result and the treatment direction may be expressed to such a degree that not only a person, such as a doctor, having specialized knowledge but also a patient may easily understand the diagnosis result and the treatment direction. That is, the patient may also directly determine the diagnosis and treatment plan, such as whether or not to visit a hospital in order to diagnose a disease or to maintain the existing treatment direction, through the self-diagnosis using the system according to an embodiment of the present disclosure.

The diagnosis and analysis frame 430 may display the result analyzed by the disease analyzer 300 as a prediction result of the anterior eye disease. The prediction result may be expressed as probability with which the corresponding anterior eye disease may occur. In addition, the disease class may be expressed as a degree of progression using predetermined numbers, as illustrated in FIG. 4. Furthermore, in FIG. 4, in addition to six categories, such as infectious inflammation, non-infectious inflammation, and non-inflammatory disease, indicated in the table of the diagnosis and analysis frame 430, the other anterior eye state prediction categories may be included. That is, the anterior eye state prediction categories may include all anterior eye states classified as the result of the diagnosis for anterior eye diseases according to the present disclosure.

However, the output unit 400 of the diagnosis system for anterior eye diseases is not limited to the configuration illustrated in FIG. 4. That is, the display form of the output unit 400 is not limited as long as various pieces of medical information, including the diagnosis result of the anterior eye disease and the disease class, may be provided to the user (e.g. a doctor or a patient). In addition, such medical information may also be provided in the form of sound to the user.

The medical information may include at least one of the current state information of the anterior eye, the future state prediction information of the anterior eye, and the treatment information of the disease class. The current state information of the anterior eye may be information including both the disease type and the disease class of the anterior eye. The future state prediction information of the anterior eye may be predicted using the machine learning model. Examples of the machine learning model for this purpose may include a recurrent neural network (RNN), a multi-layer perception (MLP), and the like. The future state prediction information may include the type and the degree of progression of the disease predicted to occur in the future depending on the current state of the anterior eye, and may include rejection predicted to occur depending on the current state. The treatment information of the disease class may include the classified anterior eye disease and treatment information according to the disease class.

For example, the current state information of the anterior eye may include keratitis classified to be a type of anterior eye disease that occurs in a surrounding portion of the cornea due to the blepharitis, and the future state prediction information of the anterior eye may include determination information indicating that the disease class corresponding to an inflammation in the surrounding portion of the cornea is predicted to be increased from 3 to 4. The treatment information may include information indicating that steroid eye drop treatment and eyelid management are required.

In addition, when the current state information of the anterior eye is determined to be keratitis that occurs in the surrounding portion of the cornea due to the herpes virus, the treatment information may include information regarding the taking of an antivirus agent or the eye-dropping of an eye bath ointment.

In another example, when the current state information of the anterior eye is determined to be bacterial keratitis caused by *Pseudomonas aeruginosa*, the future state prediction information may include information indicating the danger of the corneal perforation and the treatment information may include information indicating that the rapid eye-dropping of a broad-spectrum antibiotic eye bath ointment is required to cure the bacterial keratitis.

The diagnosis system 10 for anterior eye diseases according to an embodiment of the present disclosure may further include an anterior eye information input unit. The anterior eye state information of the patient currently having an anterior eye disease may be inputted to the anterior eye information input unit. The anterior eye state information may include information regarding the feeling of discomfort of the patient depending on the state of the anterior eye. The disease analyzer according to the present disclosure may predict the treatment result or the degree of satisfaction of the treatment according to the treatment direction presented in the present disclosure, on the basis of the input anterior eye state information and the anterior eye disease and the disease class analyzed by the disease analyzer.

For example, when the patient has the cataract, a score of discomfort depending on the current degree of the cataract of the patient may be input to the anterior eye information input unit. The disease analyzer may classify the degree of the cataract of the anterior eye in the disease class, on the basis of the anterior eye image of the cataract patient, and may present cataract surgery recommendation information, i.e. information regarding a recommendation for a cataract surgery. In addition, the degree of satisfaction of vision after the cataract surgery or a result of the surgery may be predicted, on the basis of the score of discomfort, the degree of the cataract, and the cataract surgery recommendation information.

In the diagnosis system 10 for anterior eye diseases according to an embodiment of the present disclosure, the characteristic information may include at least one of color information of the lesion, position information of the lesion, depth information of the lesion, blood vessel information of the surrounding portions of the cornea, surface information of the conjunctiva, and surface information of the sclera.

That is, the disease analyzer 300 of the diagnosis system 10 for anterior eye diseases may classify the anterior eye disease on the basis of the characteristic information extracted by the characteristic extractor 200. Specifically, the color information of the lesion may include color change information of the cornea, the conjunctiva, or the sclera. For example, when the cornea is infected, the color of the lesion may be detected to be white. In addition, the anterior eye disease may be classified according to the color information of the lesion. For example, in a picture produced by dyeing the infected cornea, a portion of the picture including the lesion may be detected to be green. Furthermore, since the anterior eye disease may be determined according to the aspect of the blood vessels in the surrounding portions of the cornea, the blood vessel information of the surrounding portions of the cornea may be used as the characteristic information. In addition, the anterior eye disease may be classified according to the surface information of the conjunctiva or the sclera, for example, the degree of roughness of the surface, such as the smoothness of the surface. Furthermore, although the anterior eye disease may be classified according to each of the pieces of the characteristic information, the anterior eye disease may be classified in consideration of two or more pieces of the characteristic information.

In the diagnosis system 10 for anterior eye diseases according to an embodiment of the present disclosure, the machine learning model of the characteristic extractor 200 may include a deep convolutional generative adversarial net (DCGAN). The output unit 400 may output both the anterior eye image 20 and the image information regarding the lesion extracted on the basis of the machine learning model.

The DCGAN is comprised of a discriminator module and a generator module. The DCGAN may correspond to a deep learning algorithm configured to generate a new anterior eye image 20 using a trained model. That is, the output unit 400 may output the image information of the lesion extracted using the DCGAN model combined with the anterior eye image 20. The image information of the extracted lesion may include the position information of the lesion. Specifically, since it may be difficult to accurately determine the position information of the lesion in some cases, the anterior eye image 20 may be used as learning data and the image of the lesion may be included in the anterior eye image 20 in order to improve the accuracy of the determination. Accordingly, the position of the lesion may be accurately extracted.

A diagnosis method using the diagnosis system 10 for anterior eye diseases according to an embodiment of the present disclosure may be provided.

Figure 5:
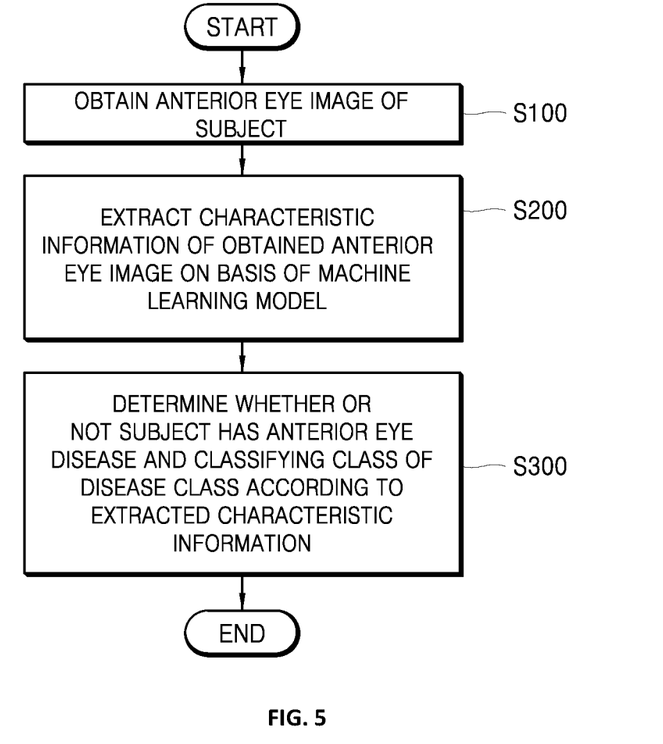
FIGS. 5 and 6 are flowcharts illustrating a diagnosis method using the diagnosis system for anterior eye diseases according to an embodiment of the present disclosure.

FIG. 5 is a flowchart illustrating a diagnosis method using the diagnosis system 10 for anterior eye diseases according to an embodiment of the present disclosure. Referring to FIG. 5, the diagnosis method may include step S100 of obtaining the anterior eye image 20 of the subject, step S200 of extracting the characteristic information of the obtained anterior eye image 20 on the basis of the machine learning model, and step S300 of determining whether or not the anterior eye of the subject has a disease and classifying the disease class according to the extracted characteristic information.

In the diagnosis method using the diagnosis system 10 for anterior eye diseases according to an embodiment of the present disclosure, the anterior eye image 20 of the subject may be obtained in real time for a diagnosis, or may be obtained by loading the anterior eye image 20 previously stored in the storage of the diagnosis system 10 for anterior eye diseases.

Figure 6:
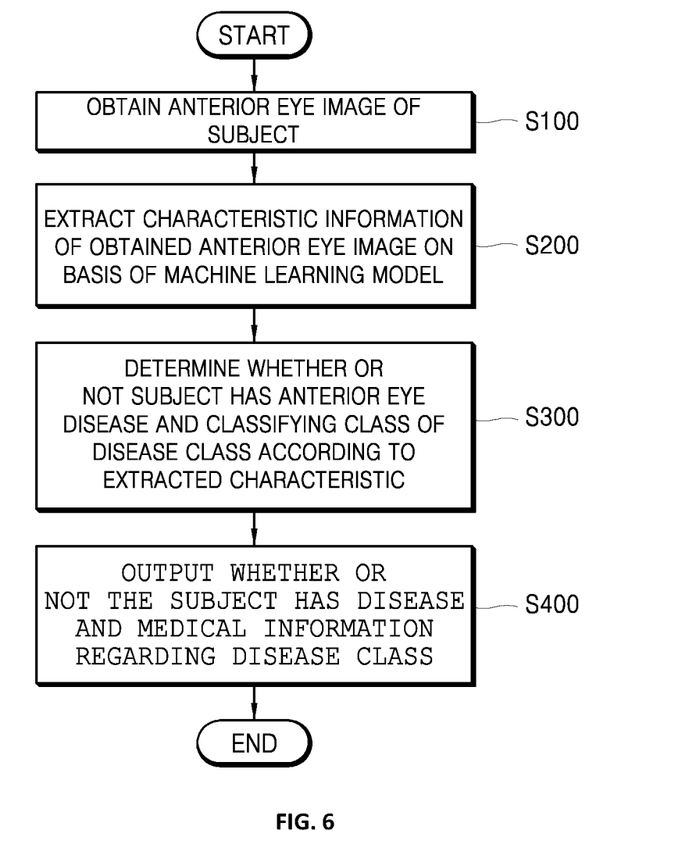

FIG. 6 is a flowchart illustrating a diagnosis method using the diagnosis system 10 for anterior eye diseases according to an embodiment of the present disclosure. Referring to FIG. 6, the diagnosis method may further include, after the step S300 of determining whether or not the anterior eye of the subject has a disease and classifying the disease class according to the extracted characteristic information and classifying the disease class, step S400 of outputting the medical information of the classified disease class through the output unit 400 of the diagnosis system 10 for anterior eye diseases.

In an embodiment of the present disclosure, a computer readable recording medium in which a program configured to realize the above-described method is recorded may be provided.

The above-described method may be written in a program that may be executed in a computer, and may be realized by a general-purpose digital computer operating the program using a computer readable medium. In addition, a structure of data used in the above-described method may be recorded in a computer readable medium via a variety of means. The recording medium, in which a computer program or codes that may be executed to perform a variety of methods of the present disclosure are recorded, should not be understood as including a temporary object, such as carrier waves or signals. The computer readable medium may include a storage medium such as a magnetic storage medium (e.g. an ROM, a floppy disk, or a hard disk) and an optical reading medium (e.g. a CD-ROM or a DVD).

The description of the present disclosure is intended for illustration, and those skilled in the art will appreciate that the present disclosure may be easily modified in other detailed forms without changing the technical spirit or essential features of the present disclosure. Therefore, the above-described embodiments should be understood as being illustrative rather than restrictive. For example, each component described as a single component may be carried out in a distributed form, and similarly, components described as being distributed may also be carried out in an integrated form.

The scope of the present disclosure should be defined by the accompanying claims rather than by the detailed description, and all changes or modifications derived from the meanings and scopes of the claims and equivalent concepts thereof should be construed as being included in the scope of the present disclosure.

What is claimed is:

1. A diagnosis system for anterior eye diseases, the diagnosis system comprising:
   an image obtainer configured to obtain an anterior eye image of the anterior eye of a subject;
   a characteristic extractor configured to extract characteristic information of the obtained anterior eye image including a machine-learning model which learns patterns of changes or aspects of changes in anterior eyes over time from a plurality of anterior eye images, wherein the characteristic extractor extracts the characteristic information by applying a plurality of filters to each of a plurality of areas of the anterior eye image and repeatedly resizing the plurality of areas to generate a feature map of the anterior eye of the subject; and
   a disease analyzer configured to determine whether or not the anterior eye of the subject has a disease and classifying a disease class according to the extracted characteristic information and the patterns or changes in the plurality of anterior images over time, and wherein the disease analyzer classifies the disease using a classification model being one of a multi-layer perceptron (MLP) of a support vector maching (SVM).

2. The diagnosis system of claim 1, further comprising a storage in which the plurality of anterior eye images are stored including previously-obtained anterior eye images of the subject and other subjects, wherein the anterior eye image of the subject is obtained in real time for a diagnosis or is obtained by loading the anterior eye image stored in the storage.

3. The diagnosis system of claim 1, further comprising an output unit configured to output medical information regarding whether or not the anterior eye of the subject has the disease and the disease class, which are determined and classified by the disease analyzer.

4. The diagnosis system of claim 3, wherein the machine-learning model of the characteristic extractor comprises a deep convolutional generative adversarial net, and
   the output unit outputs both the anterior eye image and image information regarding a lesion extracted in accordance with the machine-learning model.

5. The diagnosis system of claim 3, wherein the medical information comprises at least one of current state information of the anterior eye, future state prediction information of the anterior eye, and treatment information of the disease class.

6. The diagnosis system of claim 1, wherein the characteristic information comprises at least one of color information of a lesion, position information of the lesion, depth information of the lesion, blood vessel information of surrounding portions of cornea, surface information of conjunctiva, and surface information of sclera.

7. The diagnosis system of claim 1, wherein the image obtainer includes a slit lamp microscope.

8. A diagnosis method using a diagnosis system for anterior eye diseases, the diagnosis method comprising:
   obtaining an anterior eye image of the anterior eye of a subject;
   extracting characteristic information of the obtained anterior eye image on using a machine-learning model which learns patterns of changes or aspects of changes in anterior eyes over time from a plurality of anterior eye images, wherein extracting the characteristic information includes applying a plurality of filters to each of a plurality of areas of the anterior eye image and repeatedly resizing the plurality of areas to generate a feature map of the anterior eye of the subject; and
   determining whether or not the anterior eye of the subject has a disease and classifying a disease class according to the extracted characteristic information and the patterns or changes in the plurality of anterior images over time, and wherein the disease is classified using a classification model being one of a multi-layer perceptron (MLP) or a support vector maching (SVM).

9. The diagnosis method of claim 8, wherein the anterior eye image of the subject is obtained in real time for a diagnosis or is obtained by loading an anterior eye image previously stored in a storage of the diagnosis system for anterior eye disease.

10. The diagnosis method of claim 8, further comprising outputting, by an output unit of the diagnosis system for anterior eye diseases, medical information regarding the classified disease class after the determining and classifying.

11. A non-transitory computer readable recording medium in which a program configured to realize the method of claim 8 is recorded.

* * * * *